(12) United States Patent
Hansen

(10) Patent No.: US 9,393,196 B2
(45) Date of Patent: Jul. 19, 2016

(54) PREPARATION FOR PREVENTING OR TREATING CALCIUM DEFICIENCY CONDITIONS IN MAMMALS

(76) Inventor: Richard Brinch Hansen, Odder (DK)

( * ) Notice: Subject to any disclaimer, the term of this patent is extended or adjusted under 35 U.S.C. 154(b) by 1281 days.

(21) Appl. No.: 11/813,459

(22) PCT Filed: Jan. 6, 2006

(86) PCT No.: PCT/DK2006/000010
§ 371 (c)(1),
(2), (4) Date: Jan. 28, 2008

(87) PCT Pub. No.: WO2006/072252
PCT Pub. Date: Jul. 13, 2006

(65) Prior Publication Data
US 2008/0292666 A1 Nov. 27, 2008

(30) Foreign Application Priority Data
Jan. 7, 2005 (DK) .................................. 2005 00028

(51) Int. Cl.
| C08G 73/10 | (2006.01) |
| C08K 3/30 | (2006.01) |
| A61K 9/00 | (2006.01) |
| A61K 31/593 | (2006.01) |
| A61K 33/06 | (2006.01) |
| A61K 33/14 | (2006.01) |

(52) U.S. Cl.
CPC .............. *A61K 9/009* (2013.01); *A61K 31/593* (2013.01); *A61K 33/06* (2013.01); *A61K 33/14* (2013.01)

(58) Field of Classification Search
USPC ................................................ 524/323, 418
See application file for complete search history.

(56) References Cited

U.S. PATENT DOCUMENTS

| 4,346,077 A | | 8/1982 | Braund et al. | |
| 4,621,763 A | * | 11/1986 | Brauner | .......................... 229/5.5 |
| 4,835,142 A | * | 5/1989 | Suzuki et al. | ..................... 514/53 |
| 4,931,290 A | | 6/1990 | Rebhan | |
| 5,007,579 A | * | 4/1991 | Thomas, Jr. | .................... 229/5.5 |
| 5,395,622 A | | 3/1995 | Nielsen | |
| 5,560,920 A | | 10/1996 | Goff et al. | |
| 6,214,378 B1 | * | 4/2001 | Tanida et al. | ................. 424/463 |
| 6,322,821 B1 | | 11/2001 | Register | |

FOREIGN PATENT DOCUMENTS

| SE | 461567 | | 3/1990 | |
| WO | WO-90/07338 | | 7/1990 | |
| WO | WO 95/08321 | * | 3/1995 | ............... A61K 9/48 |
| WO | WO-95/08321 | | 3/1995 | |
| WO | WO-98/40050 | | 9/1998 | |

OTHER PUBLICATIONS

Bethard. www.vetmed.wisc.edu/dms/fapm/fapmtools/2nutr/calciumgel.pdf. Archived Feb. 28, 2003.*
Oetzel. www.vetmed.wisc.edu/dms/fapm/fapmtools/2nutr/calciumgel.pdf . Published online Feb. 28, 2003.*
Milk Fever in Dairy Cows. http://www.mad-cow.org/~tom/marsh__milkfever.html. Published on Jul. 23, 1996.*
Pherson. Journal of Dairy Science vol. 81, No. 7, 1998.*
Quiz Bowl. http://web.ics.purdue.edu/~rallrich/questions.html. Accessed Jul. 16, 2010.*
Alzahal.J. Anim Sci. AlZahal et al. 85 (1): 213.*
Cummings. Gut 1987 28: 1221-1227.*
J.P. Goff and R.L. Horst Oral administration of Calcium Salts for Treatment of Hypocalcemia in Cattle vol. 76, No. 1 pp. 101-108.
A Comparative Study of the Effectiveness of Calcium Propionate and Calcium Chloride for the prevention of Parturient Paresis in Dairy Cows, vol. 81 No. 7, 1998, pp. 2011-2016.
R. J. Jorgensen and A. Basse , Dansk , Calciumklorid til Koer Bivirkninger efter peroral indgivelse—En forelobig meddelelse, 1990, 73: 140-141.
Bo Pehrson and Goran Jonsson, Risikoen for bivirkninger of peroralt tilforte kalciumsalte til malkekoer, 1990, 73: 653-655.
Bo Pehrson, Margarita Jonsson, and Goran Jonsson, Forsok att forebygga kalvnings-forlamning genom peroral till-forsel av inkapslade Ca-salter, 1989, 41, 15: 923-927.

* cited by examiner

*Primary Examiner* — Adam C Milligan
(74) *Attorney, Agent, or Firm* — Browdy and Neimark, PLLC

(57) ABSTRACT

An essentially dry powdered preparation containing a calcium source for the prevention and treatment of calcium deficiency conditions in mammals, e.g. dairy cows, is enclosed in a substantially water soluble, dispersible or disintegrable casing mainly composed of a cellulose material such as e.g. paperboard, cardboard, millboard, or pasteboard, or a gelatinized starch material. The calcium source is preferably a mixture of calcium chloride and calcium propionate enclosed in a cylindrical paperboard or cardboard tube or a gelatinized starch shell closed at both ends, which is administered to an animal with a bolus or bullet gun. The administration is safe and clean and the powdered mixture is quickly released in the stomach or rumen without causing erosion, irritation or inflammation of the mucosa.

17 Claims, 3 Drawing Sheets

PREPARATION FOR PREVENTING OR TREATING CALCIUM DEFICIENCY CONDITIONS IN MAMMALS

The present invention relates to compositions and means for preventing and/or treating calcium deficiency conditions (hypocalcaemia), e.g. milk fever (Parturient Paresis), in mammals in general, especially ruminants, more particular dairy cows.

BACKGROUND OF THE INVENTION

Hypocalcaemia is a disorder frequently met in mammals, in particular ruminants, especially dairy cows, in connection with the females' delivery (parturition) and is then called milk fever or Parturient Paresis. It is caused by a decline of the calcium concentration in the blood plasma prior to, during and/or after delivery, because the onset of lactation, i.e. the beginning milk production in the mammary glands of the udder requires calcium, which is extracted from the extracellular fluid pool, in particular the bloodstream. If the removed calcium is not immediately replenished by either intestinal calcium absorption or by bone calcium resorption, the calcium extraction leads to a decline of the plasma calcium concentration. In particular in dairy cows the demand for calcium in the udder is high in connection with calving in order to produce the colostrum. If the calcium extraction for the milk production in the udder of the cow exceeds the actual calcium supply, hypocalcaemia occurs, which, if untreated, in turn leads to decreased ruminal function, displaced abomasums, slow calving, retained placenta, downer cow syndrome, uterine prolapse, metritis, and finally death.

The normal blood plasma calcium level in cattle is about 1.25 mM, at about 1 mM reduced ruminal function occurs, milk fever occurs below about 0.5 mM, and a further decline to 0.4 mM causes death. Milk fever appears shortly prior to, during or relatively soon after calving; 75% of the incidences appear within 24 h after calving.

The prevalence of milk fever for dairy cows after first and second calving is low, i.e. 0-2%, but is high, i.e. 5-8 and 12-14% for third and fourth calving cows, respectively (ref: "Jerseybladet" June 1996). The increasing prevalence relative to the number of calving is probably a consequence of the demand for high milk producing capacity of present-days dairy cows. Consequently, as modern dairy industry requires a constant high milk yield prevention and treatment of milk fever is an economical important issue.

As the progression of milk fever and other hypocalcaemia related conditions and diseases is fast, the administration of calcium for prevention and treatment has to be fast too.

Thus, the hyper acute treatment of milk fever is only practicable by intra venous administration of a calcium solution, which is to be administered by a veterinarian. In less acute incidents and for prevention purposes, oral administration is a more convenient and cost effective way to administer the necessary calcium supply, which can be given by the farmer himself or a skilled farm-worker.

PRIOR ART

During the course of time several products for oral administration of calcium for the prevention and treatment of milk fever and hypocalcaemia have been suggested.

Thus, the effect of oral administrable products based on compositions comprising $CaCl_2$ and/or other calcium compounds, e.g. $CaCO_3$, $CaSO_4$, Ca-acetate, Ca-lactate, Ca-levulinate, Ca-propionate and others, have been investigated. These compositions may be mixtures comprising one or more calcium compound(s), other minerals, vitamins, additives, carriers and excipients. The compositions have been in liquid, half solid (gels) or solid forms.

Due to its high calcium content, high solubility in the ruminal juice of cattle and quick entrance into the bloodstream from the digestive tract, $CaCl_2$ has for long been the most widely used calcium compound for the prevention and treatment of hypocalcaemia. But $CaCl_2$ does not taste well and therefore the cows refuse to ingest it orally more than once, for the reason of which use of force applied to the animal is often necessary for the following doses required for the complete treatment. Besides, the Cl-ions may cause a lowering effect on blood plasma pH, which can lead to metabolic acidosis that requires supplementary i.v. treatment(s) (Goff, J. P. and Horst, R. L., *J Dairy Sci.*, 1993, 76: 101-108).

Attempts have been made to solve the problems related to oral administration of $CaCl_2$. Thus, it has been tried to mask the bad taste of calcium chloride by formulating it into a gel comprising hydroxycellulose and/or propylene glycol as gel matrix and sweetening agent, but Jørgensen, R. J. and Basse, A., *Dansk Vet. Tidsskr.*, 1990, 73: 140-141, reported that such aqueous gel formulations may cause severe mucosa erosion in the rumen of the cow when they are administered orally as 400 mL dose ingestions, presumably because the gels are heavy and slowly disintegrable and therefore tend to be deposited as an immobile concentrated bolus in the rumen for a long period of time before they slowly dissolve and dilute in the total volume of the rumen.

It has also been tried to formulate calcium chloride preparations as aqueous emulsions in vegetable oil, e.g. soybean oil, and Jørgensen, R. J. and Basse, supra, reported that such emulsions did not cause severe mucosa erosion in the rumen, but only superficial injuries and mild clinical symptoms in the form of reduced appetite for 1-2 days. However, Goff, J. P. and Horst, supra, found that vegetable oil emulsions of calcium chloride were poorly absorbed and did not increase plasma Ca-concentration statistically significantly over pre-treatment concentrations at any time within an observation period of six hours after ingestion. This poor absorption result was believed to be due to the formation of sparely soluble calcium soaps.

Nielson, Leif H. reports in U.S. Pat. No. 5,395,622 that attempts have also been made to treat animals suffering from milk fever with capsules containing powdery calcium acetochloride, but that the calcium content of such capsules is relatively low so that a considerable number (e.g. 16) of capsules should be administered to the sick animal at two hours intervals, which render the preparation unsuitable for practical use. Instead the author suggests to produce a solid dosage unit in the form of a bullet by preparing an aqueous pumpable mixture of $CaCl_2.6H_2O$ and plaster, i.e. $CaSO_4.\frac{1}{2}H_2O$, and casting and solidifying the mixture in a plurality of moulds. Optionally the solid bullets are encapsulated within individual gelatine capsules. Such solid bullet dosage units have been commercially available for years sold under the trade name BoviKalc®. Each bullet has the form of a cylinder having a length of about 140 mm and a diameter of about 34 mm and weighing about 196 gram, of which 57.9% is $CaCl_2.6H_2O$, 23.2% is $CaSO_4.\frac{1}{2}H_2O$, 14.4% is water, and 4.5% is glyceryl PEG ricinoleate (coating material). Thus, each bullet contains about 43 gram of total calcium, of which approximately 31 gram is present as calcium chloride and approximately 12 gram is present as calcium sulphate.—The bullet is administered with a bullet gun delivering it into the oesophagus of the animal, which swallow the bullet into the rumen without risk for inhalation into the respiratory tract and lungs.

Pehrson, Bo, Jonsson, Margarita, and Jönsson, Göran, *Svensk Veterinärtidning,* 1989, 41, 15: 923-927, reported a comparative study of the use of such solid calcium chloride/calcium sulphate cylinders and a calcium chloride/hydroxycellulose gel in preventing milk fever in dairy cows previously treated against this order in connection with calving and found no significant difference between the beneficial effects of the two treatment agents. However, Pehrson, Bo and Jönsson, Göran, *Dansk Vet. Tidsskr.* 1990, 73: 653-655, reported subsequently that also administration of solid calcium chloride/calcium sulphate cylinders could cause severe mucosa erosion and inflammatory conditions in the rumen of cows corresponding to what was found by Jørgensen and Basse (supra) after the administration of a 400 ml dose of aqueous calcium chloride gel. Pehrson and Jönsson assumed that the erosive and inflammatory reaction in the rumen was a consequence of the concentrated salts leaching out from the cylinders being placed rather immobile in the rumen while it is disintegrating and dissolving there.

Thus, solid bullets of calcium chloride and calcium sulphate appear to present the same physiological drawbacks as aqueous calcium chloride gels. Besides, the production of the solid calcium chloride/calcium sulphate bullets are rather complicated and time consuming because dry powders of calcium chloride and calcium sulphate hemi hydrate first have to be mixed thoroughly, then mixed thoroughly with water and subsequently poured into gelatine capsules or cast forms and then allowed to solidify and harden for about typically 24 hours at room temperature in an airtight compartment. If not encapsulated in gelatine capsules the bullets would subsequently have to be coated with e.g. a fatty acid mixture or glyceryl PEG ricinoleate in order to be easily swallowed by the cow when introduced into its oesophagus.

Goff, J. P., and Horst, R. L., 1993 "Oral administration of Ca salts for treatment of hypocalcaemia in cattle", *J Dairy Sci.,* 76: 101-108, reported a comparative investigation of oral administration of aqueous solutions or slurries of calcium chloride, calcium propionate, and calcium carbonate on the serum calcium level in cows. It was found that calcium chloride solution drenches increased blood Ca-concentrations more quickly than did Ca-propionate, but the Ca-propionate effects lasted longer, whereas calcium carbonate drenches were ineffective. It was further found that oral administration of 50 g. of Ca as $CaCl_2$ raised plasma Ca-concentrations to the same extent as 4g. of Ca as $CaCl_2$ given i.v., but that the total amount of $CaCl_2$ administered in 24 h should not exceed 288 g (120 g of Ca) to avoid induction of severe metabolic acidosis. Finally it was concluded that development of a Ca-propionate gel or mixture of Ca-propionate with $CaCl_2$ may admit more Ca to be administered without risk of metabolic acidosis, but there is neither guidance nor hint of how to formulate such a mixture or how to administer it.

Later Goff, J. P., and Horst, R. L. disclosed in U.S. Pat. No. 5,560,922, filed Apr. 7, 1995, the preparation of a calcium propionate paste and its use for treatment of milk fever. The paste was prepared by mixing calcium propionate and propylene glycol with either citric acid or phosphoric acid in an amount of about 7-9% by weight of the total composition. The paste was placed in an ejection tube and administered to a cow with a caulk gun. Tests performed with this paste showed that 75 g. of calcium as calcium propionate did not increase plasma calcium as rapidly as 75 g. calcium as $CaCl_2$ in a corresponding paste, but the increase in plasma calcium was sustained for a longer period with calcium propionate. However, no attempts were made to combine calcium propionate and calcium chloride in one and the same paste.

Pehrson, B., Svensson, C., and Jönsson, M., *J. Dairy Sci.,* 1998, 81: 2011-2016, performed a comparative study of the effectiveness of calcium propionate and calcium chloride for the prevention of parturient paresis in dairy cows. The calcium chloride was administered as a commercially available oily solution (lycine oil; Paragel vet; Pherrovet AB, Malmö, Sweden), whereas the calcium propionate was administered as cylinders that were 15 cm long and 3.4 cm in diameter and each containing 20 g. of calcium. It was impossible physically to incorporate more than 20 g of calcium in a bolus of a size that could be easily administered to a cow. Pehrson et al do not disclose how each cylinder of calcium propionate is produced, but only that it is administered to the cow with a balling gun. Pehrson et al. concluded that treatment with calcium propionate was as effective in the prevention of milk fever as was treatment with calcium chloride, even though cows given calcium propionate received only 120 g of calcium compared with the 216 g received by cows treated with calcium chloride. However, in order to administer the only 120 g of calcium as calcium propionate it was necessary to administer six boluses of calcium propionate instead of just four doses administrations of the oily calcium chloride solution. This fact makes this calcium propionate approach more cumbersome and laborious in practice, which may be one of the reasons why it has not yet been used commercially in spite of the fact that calcium propionate does not have any bitter taste, neither cause erosive or inflammatory effects in the rumen nor dangerous acidosis in the blood of the treated animals.

Finally WO 95/08321 discloses a capsule for introducing drugs into the proventriculi of cattle, which is made of a tube of cardboard or similar fibre material with a filling of the drug either in admixture with a fatty material, which is meltable by the body heat of the animal upon oral administration of the capsule, or contained in a space between end plugs of such a fatty material. The tube per se remains open and may further be cut over at least a partial axial length or be made of a rounded sheet blank so as to present an axial slit. However, the production of such capsule is cumbersome, time-consuming and expensive and the drug material will either initially be impregnated with the fatty material or later be enveloped in a fatty or greasy film when the end plugs of fatty material melts in the stomach of an animal. In both cases this will hamper the quick absorption of an optional calcium source from the stomach or rumen of an animal in which the capsule is ingested.

Thus, currently there are mainly four different types of commercial calcium products available for orally preventing and/or treating milk fever in dairy cows at the period of time about their calving, viz.:

1. Long-necked bottles containing typically 500 mL gel product of either calcium propionate/calcium acetate or calcium chloride,
2. Drench-dose liquids delivered typically in an amount of 230-250 mL of a calcium solution with a drench gun,
3. Pasta-tubes containing typically 500 mL of a calcium compound paste, and
4. Cylindrical calcium-bullets comprising calcium chloride embedded in a calcium sulphate (gypsum) matrix to be delivered with a bullet gun, which, by the administration of four boluses, provide the necessary calcium supplement. But all these products suffer from one or more of the different drawbacks described above or are associated with administration problems such as slow ingestion in order to minimize the animals' risk of aspiration of the liquid or semi liquid products or spillage of the same and contamination of the hands and clothes of the administrator.

Therefore, there is still a need for a calcium supplemental product, which can be produced in a simple and inexpensive manner and which can be administered orally as a bolus to an animal in a simple, safe, quick and clean manner without unduly struggle with the animal and causing no or only minor, harmless uncomfortable effects on the animal and still be at least as effective or even better than the products used hitherto.

Such calcium supplemental product has now been provided with the present invention, which in a first aspect provides a new means for administrating a solid bolus of a calcium source and which in a second aspect provides a novel composition of such calcium sources.

SUMMARY OF THE INVENTION

The above objects are obtained with the preparation of the invention comprising a calcium source for the prevention and treatment of calcium deficiency in mammals, said preparation being characterised in that it is in an essentially dry non-fatty powdered form and is enclosed in a substantially water soluble, dispersible or disintegrable casing mainly composed of cellulose or gelatinized starch material. The preparation is particularly usable for ruminants, in particular dairy cows. Preferably the preparation is completely encapsulated in the casing, i.e. the casing is closed and/or sealed after the introduction of the preparation into the casing.

That the preparation is essentially dry does not imply that it may not contain moist or water, e.g. crystal water, at all, but that the total content of such moist or water will not tend to dissolve or disintegrate or in other manner be harmful to the casing during storage and distribution of the preparation.

That the preparation is in an essentially non-fatty powdered form means that the individual powder particles is at least not enveloped in or impregnated with any fatty or greasy substance to an extent that will hamper the calcium source to quickly dissolve or leach into the gastric or ruminal juice of an animal when ingested. However, preferably the powdered preparation is essentially completely free of any fatty or greasy substance.

By enclosing an essentially dry preparation containing a calcium source in a casing composed of mainly cellulose or gelatinized starch material, which is substantially water soluble, dispersible or disintegrable, it is possible to administer a rather large dose of calcium to an animal, in particular a dairy cow, with a bullet gun in a simple, safe, quick and clean manner without any risk for spillage or inspiration into the trachea and lungs of the animal of any administered material and nor will the animal feel any bad taste. On the other hand, the calcium source of the preparation will be ready available in the stomach, e.g. the rumen, of an animal because the cellulose or starch casing quickly will dissolve and/or disintegrate in the gastric or ruminal juice exposing its content for the gastric or ruminal juice.

When the calcium containing preparation is in a powdered non-fatty form the preparation will very quickly dissolve or disintegrate into the gastric or ruminal juice and be spread in the total lumen or volume of the stomach or rumen, when ingested, so there will be no or very little risk for erosive or irritative effects on the mucosa of the stomach even though some of the constituents of the preparation might have such capacity per se in concentrated form.

Besides, the preparation according to the invention can be produced in a very simple and inexpensive manner as will be explained in more details below and in the detailed part of the description of the invention.

The water soluble or disintegrable cellulose casing is not necessary composed of cellulose material alone, but may comprise other digestible or non-digestible, but harmless materials such as lignin and usual paper-making non-toxic chemicals. Thus, the casing may be prepared from e.g. water absorbent paperboard, cardboard, millboard, or pasteboard, which may be non-sized or sized with a water soluble edible size. Such cellulose casing may also be stratified or laminated. Preferably the casing wall is thin and quickly soluble, dispersible or disintegrable in the gastric or ruminal juice of an animal.

However, the casing may also be composed of an edible gelatinized starch material. Such gelatinized starch casing can be produced by extruding a hollow cylinder or shell from a gelatinizable material, e.g. wheat, rice or potato flour, by a particular gelatinization process making it first plastic and then hard and impervious, but still soluble, dispersible or disintegrable in water and/or the gastric or ruminal juice of an animal. Optionally the gelatinized starch casing may also be produced by coating a massive core of the calcium containing preparation with the gelatinized starch material in the plastic state, e.g. by extrusion coating a core cylinder of the preparation material with gelatinized starch and fusing and closing the coating thus produced at the ends of the cylinder. The finished cylinder shell or capsule should preferably not have any sharp edges or pointed corners.

Preferably the casing is provided with at least one weakening line susceptible to be quickly broken in the gastric or ruminal juice of an animal. This feature will cause quick opening of the casing after it has entered into the stomach or rumen of an animal and the casing will then be attacked by the gastric juice from both its outside and inside and consequently be broken down more quickly. Besides, the preparation in the casing will begin leaving the casing through the opening produced in the casing immediately when the weakening line is broken.

In a preferred embodiment the casing has the form of a capsule or shell, e.g. a cylindrical tube, which is closed at each end with a cap or a disk of cellulose material, e.g. water absorbent cardboard. The end caps or disks may also be produced of e.g. gelatinized starch. When introduced into the stomach or rumen of an animal the closing caps or disks will rather soon become disintegrated in the gastric or ruminal juice, e.g. within about 20-30 minutes, which will open one or both ends of the cylindrical tube and thus give access to the interior of the tube and its content for the gastric juice.

Preferably the cylindrical tube will be provided with at least one weakening line circumferentially around its periphery. Such weakening line may be formed by a milled or cut groove or an array of perforation points or narrow slots. However, it may also be provided by constructing the tube from two parts which are connected with a water soluble or disintegrable paper tape glued to the inside and/or outside periphery of the tube along the abutting edges of the two tube sections. Also the end caps or disks may be provided with perforation points or narrow slots.

The preparation containing the calcium source is preferably in a powdered non-fatty form. Such powdered preparation is preferably compacted or compressed so that more material can be contained in the lumen of the casing. In this case it is essential that the weakening line is circumferential and not longitudinal or axial because a longitudinal weakening line will easily be split when a powdered material is compressed or compacted in a thin-walled casing during its production and the powdered material will be forced out of the split casing.

The calcium source of the preparation may in principle comprise any material capable of liberating calcium ions in contact with the gastric or ruminal juice of an animal. Preferably the preparation does only or mainly consist of one or more calcium compounds. Thus, preferably the preparation is mainly or essentially only a mixture of calcium chloride and calcium propionate. Such mixture is advantageous because calcium chloride has a high proportion of calcium (28.5% by weight), is inexpensive and ensures a high uptake rate of calcium from the stomach to the blood circulation.

Calcium propionate has a lower proportion of calcium (about 23% by weight) and lower uptake rate, but ensures a more persistent calcium level in the blood after its administration and is completely harmless to the mucosa of the stomach and other intestinal tissues.

Thus, the dilution of calcium chloride with calcium propionate in the composition of the invention ensures that the concentration of the aggressive calcium chloride will be lower at any point and at any time in the stomach (rumen) of an animal to which the preparation of the invention is administered than if pure calcium chloride were administered alone.

Hence, the risk for erosion, irritation or inflammation of the mucosa of the stomach is lowered considerably without detracting essentially from the uptake rate and level of calcium from the stomach to the blood circulation. Besides, the possibility for metabolic acidosis will also be decreased because there will be a lower uptake of Cl-ions for the same uptake level of calcium to the blood circulation. These proportions provide an optimum balance between the advantageous characteristics of calcium chloride and calcium propionate mentioned above.

The proportion of calcium chloride to calcium propionate may vary widely, but ranges generally from 10-99% by weight of calcium chloride to 90-1% by weight of calcium propionate, preferably from 50-95% by weight of calcium chloride to 50-5% by weight of calcium propionate, of the total mixture of calcium chloride and calcium propionate. More preferably the proportion of calcium chloride is about 70-90%, e.g. 80%, by weight and the proportion of calcium propionate is about 30-10%, e.g. 20%, by weight of the total calcium chloride and calcium propionate mixture.

Preferably the preparation contains at least 30 gram of calcium, more preferably at least 35 gram of calcium, and most preferably at least 40 gram of calcium per casing or capsule.

The preparation according to the invention may comprise other calcium compounds than a mixture of calcium chloride and calcium propionate, e.g. $CaCO_3$, $CaSO_4$, Ca-acetate, Ca-lactate, and others. It may further comprise other minerals, vitamins, additives, carriers and excipients. In particular the preparation may comprise a magnesium compound, e.g. MgO or $MgSO_4$, and vitamin $D_3$.

The invention also relates to a use of the preparation according to the invention for the prevention and/or treatment of milk fever (Parturient Paresis) in mammals, in particular ruminants, more especially dairy cows.

Other preferred embodiments of the invention are defined in the dependent claims.

Further advantageous features and details of the invention will appear from the following detailed description of the invention with reference to the drawings.

BRIEF DESCRIPTION OF THE DRAWINGS

Preferred embodiments of the invention are described below and depicted in the drawings, wherein.

DETAILED DESCRIPTION OF PREFERRED EMBODIMENTS OF THE INVENTION

Figure 1:
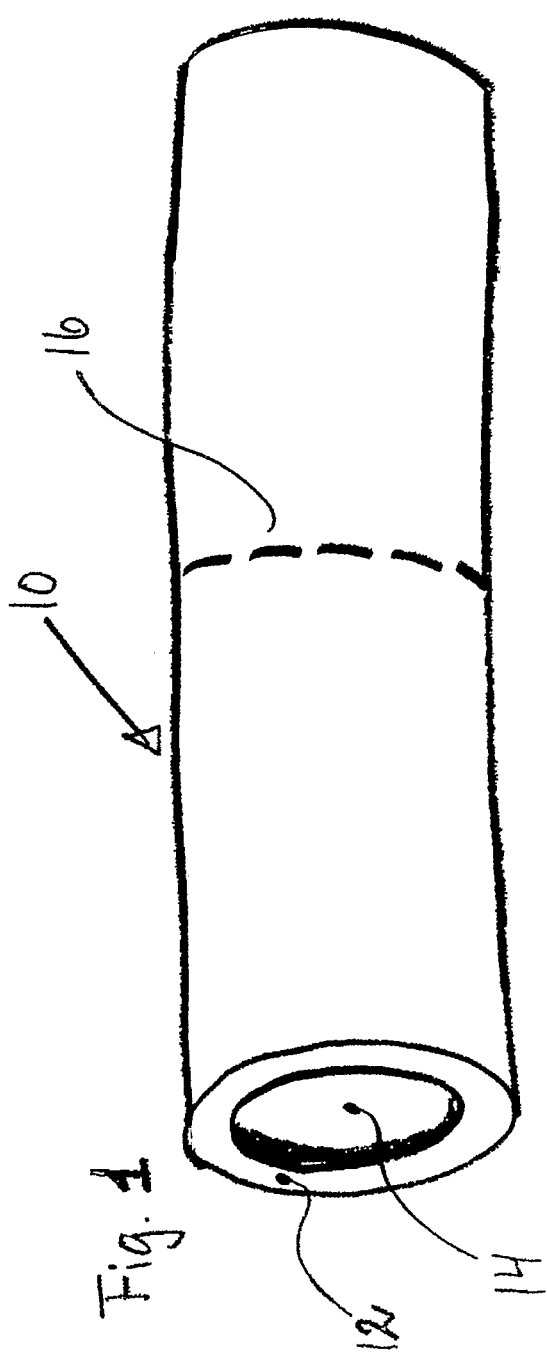
FIG. 1 is a perspective view of a preferred embodiment of the casing or capsule according to the invention having the form of a cylindrical tube.

Reference is made to FIG. 1 which is a perspective view of a preferred embodiment of the casing or capsule used for the preparation according to the invention. 10 Designates a cylindrical tube mainly composed of a water soluble, dispersible or disintegrable cellulose material, such as e.g. millboard, cardboard or pasteboard, which may be non-sized or sized with a water soluble edible size. The wall thickness of the tube may vary, but is preferably about 1 mm. Also the external diameter and length of the tube may vary, but are in preferred embodiments about 30-34 mm and 130-175 mm, respectively.

12 Designates the extreme rim of the one end of the tube, which is bended or beaded inwards so as to provide a rounded outer end edge of the tube and an inner bead or ledge. The length of the inward bended rim of the tube depends on the wall thickness of the tube, but is preferably about 4-8 mm. The bending is performed by the action of heat and mechanical pressure with an appropriate tool in a manner known per se. The other end of the tube may be bended or beaded inwards in the same manner, but is preferably leaved straight and non-bended.

14 Designates a circular disk made of water absorbent cellulose material, e.g. millboard, cardboard or pasteboard, having an area weight of e.g. about 240-350 g/m². The disk rests on the inner bead or ledge and closes the end of the tube. Preferably, the disk 14 has a diameter which is slightly greater, e.g. about 1 mm, than the inner diameter of the cylindrical tube so that when the disk 14 is inserted into the bore of the tube it will inherently be maintained therein by the elastically force produced by the compression and deformation of the disk and exerted at the abutting periphery of the disk along the inner periphery of the tube 16 Designates a weakening line made in the wall of the tube circumferentially around the periphery of the tube. Such weakening line may be in the form of a milled or cut groove in the wall of the tube making the wall thickness in the bottom of the groove substantially smaller than the wall thickness of the surrounding tube, e.g. about or less than the half thereof. However, preferably the weakening line is produced by an array of perforation points or narrow slots penetrating the total thickness of the wall or nearly penetrating the wall thickness. In order to maintain the tube sufficiently strong and intact during its production and subsequent handling of the preparation according to the invention, 20-40% of the periphery in the weakening line is left intact, i.e. 60-80% of the periphery in the weakening line is cut with a perforation blade. However, the weakening line may also be provided by cutting the tube circumferentially in two parts which are subsequently connected again with a water soluble or disintegrable paper tape or banderol glued to the inside and/or outside periphery of the tube along the abutting edges of the two tube sections.

Figure 2:
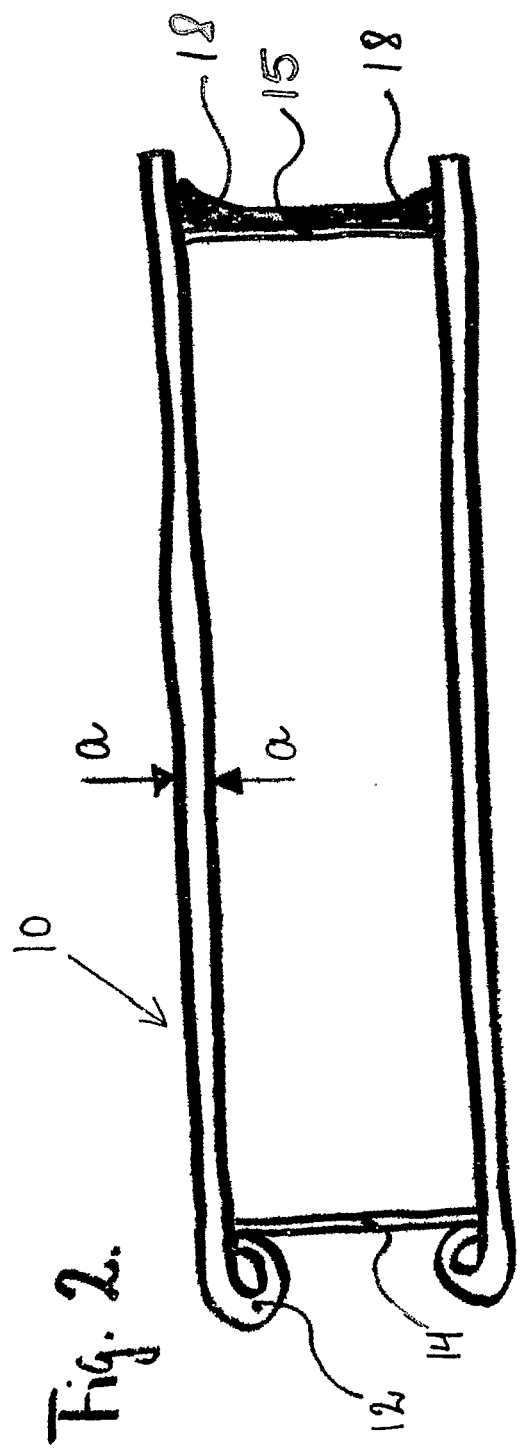
FIG. 2 is a longitudinal section through the central axis of the cylindrical tube shown in FIG. 1.

Reference is now made to FIG. 2 which shows a longitudinal section through the central axis of the cylindrical tube shown in FIG. 1. The reference numerals 10, 12, and 14 have the same meanings as explained for FIG. 1 and need not to be further detailed here. The arrows a-a designate the wall thickness of the tube as specified for FIG. 1.

15 Designates a disk at the other end of the tube corresponding essentially to the disk 14 at the former end of the tube. Also, the disk 15 has preferably a diameter which is slightly greater, e.g. about 1 mm, than the inner diameter of the cylindrical tube so that when the disk 15 is inserted into the bore of the tube it will inherently be maintained therein by the elastically force produced by the compression and deformation of the disk and exerted at the periphery of the disk along the abutting inner periphery of the tube.

18 Designates a sealing provided on the outside of the disk at its periphery and the rim on the inner side of the tube along the periphery of the disk 15. This sealing may be made of e.g. wax, paraffin or a water soluble edible glue or other harmless adhesive material.

When producing a preparation according to the invention a tube as shown in FIG. 1 and FIG. 2 is provided with the one end having an inner bead or ledge closed with a disk 14. The tube is then filled through its open end with a powdered non-fatty composition containing a calcium source, e.g. a powdered mixture essentially consisting of calcium chloride and calcium propionate. The powdered composition, e.g. 100-150 g of a powdered mixture, is then compacted and compressed with a piston in order to obtain a maximum of calcium content. Next, the disk 15 is inserted into the open end of the tube and pressed against the compacted powder composition and is then sealed on its outside along its periphery to the inside rim of the tube and is then ready for packaging and storage or shipment. Preferably the finished preparation is packaged in moisture tight bags or containers of e.g. plastic material, each package containing e.g. four cylinders.

In use a package containing a preparation according to the invention is broken and a tube is placed in a standard bolus or bullet gun, the barrel of which has an inner diameter slightly greater than the outer diameter of the cylindrical tube, e.g. 35 mm, (such as that used for BoviKalc cylinders). The sharp end edge of the tube is placed at the bottom of the barrel of the gun so that the rounded end of the tube points forward. The open barrel end of the gun is then introduced into the mouth of the animal to be treated and pushed into the pharynx beyond the root of the tongue, which will cause the animal to perform a swallowing movement during which the cylindrical tube is pushed into the oesophagus by an appropriate actuation of the piston rod. The preparation cylinder will then easily pass into the stomach or rumen of the animal without in any manner to be harmful or uncomfortable to the animal.

The gastric or ruminal juice in the stomach or rumen having a temperature of about 37° C. and a pH of about 6.7 will penetrate the circumferential weakening line and dissolve or disintegrate the remaining material of the wall along the periphery of the cylinder along the weakening line which will cause an opening and breaking of the cylinder along the line. Simultaneously the water absorbent closing disk in the beaded end of the cylinder will dissolve or disintegrate so that the cylinder will become open after about 30-40 minutes in the gastric or ruminal juice. This will cause the calcium containing preparation to be released into the gastric or ruminal juice as a multitude of individual small particles. The cylindrical tube will then become attacked from both the outside and inner side by the gastric or ruminal juice and gradually become completely dissolved or decomposed as the calcium containing composition is released. The cylindrical tube will be completely disintegrated or dissolved within about 40-60 minutes. However, it should be noted that during all the decomposition process the bolus of calcium salt(s) will be maintained in the cylindrical tube from which it is gradually released into the gastric juice so that there will be no direct contact between the mucosa of the stomach and a great bolus of concentrated calcium salt(s). Therefore, there will be no or very little risk for erosion or irritation of the mucosa in the stomach.

Figure 3:
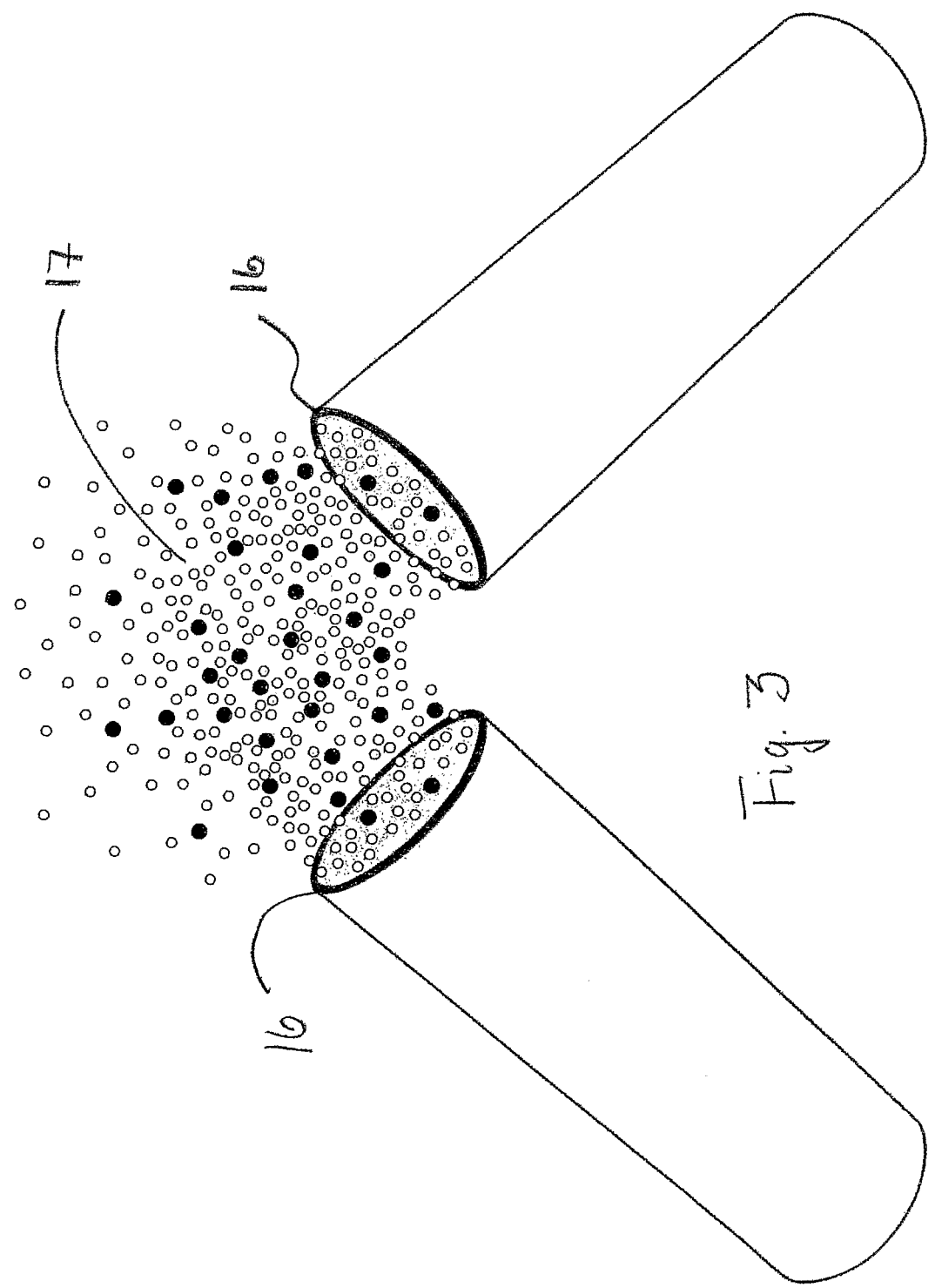
FIG. 3 is a perspective view of the cylindrical tube shown in FIG. 1 divided into two parts along a circumferential weakening line at the middle of the tube.

Reference is made to FIG. 3 which is a perspective view of the cylindrical tube illustrated in FIGS. 1 and 2 broken into two parts along the circumferential weakening line 16. It is clearly illustrated how a powdered mixture 17 of calcium chloride and calcium propionate gradually is released from the open ends of the two tube sections into the gastric environment without producing a bolus of calcium salts coming into direct contact with the mucosa of the stomach of the animal.

EXAMPLE

A cylindrical tube was produced from pasteboard (1 mm×34 mm×165 mm) sized with a water soluble edible size. The extreme rim (about 6 mm) at the one end of the tube was bended and beaded inwards so as to produce an internal ledge in that end of the tube. A circular disk of about the same diameter as the inner diameter of the tube was prepared from water absorbent pasteboard (240-350 $g/m^2$) and then introduced into the other open end of the tube and pushed through and pressed against the ledge in the former end so as to close it.

Then the void volume of the cylindrical tube was filled with 125 g of a powdered mixture of calcium chloride (90% by weight) and calcium propionate (10% by weight) providing about 35 g. of calcium and 110 mg of magnesium (provided with the calcium chloride). Next, the powdered mixture in the tube was compacted and compressed to minimize its volume and maximize the calcium content. Addition of more mixture and optimum compaction may easily bring about the calcium content in a single tube up to about 38-43 g. of calcium.

After filling, the other open end of the cylinder was closed with a pasteboard disk (240-350 $g/m^2$) having a diameter of about 1 mm greater than the inner diameter of the cylinder and the pasteboard disk was secured with a wax sealing along its periphery to the inside rim of the tube so as to be maintained fixed in and tighten the tube.

The finished tube was placed in a large glass beaker containing 37° C. hot water adjusted to a pH of 6.5 with lactic acid, which is the same temperature and acidity as in the rumen of a cow. The water in the beaker was not stirred.

The tube in the beaker was observed continuously and after 20 minutes the white paper layer on the outer side of the tube released and fell down. After about 30 minutes the bended bead (which is subjected to internal stress) began to turn inside out. 45-60 Minutes after the immersion in water a hole was formed in the beaded end of the tube and simultaneously the perforated weakening line broke and the tube was divided into two halves.

It is believed that the decomposition process described above will run faster in the stomach or rumen of an animal because in that case the process will also involve bacterial and enzymatically action and there will be some peristaltic movement of the gastric or ruminal juice and hence also of the tube in the stomach or rumen due to the periodical contraction of the latters.

Having thus described the invention in general and in more details in connection with preferred embodiments thereof it will be understood that various modifications can be made to the embodiments disclosed herein without departing from the scope of the invention as defined by the appended claims.

The invention claimed is:

1. A preparation comprising a calcium source and a casing enclosing said calcium source, which preparation can be administered orally as to bolus an animal for the prevention an/or treatment of calcium deficiency in mammals, wherein
   (1) said calcium source is
      in an essentially dry and essentially non-fatty powdered form, and
      comprises a compacted or compressed mixture of calcium chloride and calcium propionate containing at least 30 grams of calcium,
   (2) the total content of moisture or water of said powdered calcium source will not tend to dissolve or disintegrate the casing during storage and distribution of the preparation,
   (3) the individual particles of said powdered calcium source are not enveloped in or impregnated with any fatty or greasy substance to an extent that will hamper the calcium source from quickly dissolving or leaching into the gastric or rumen juice of an animal, when ingested, and
   (4) said casing is cylindrical in form and is mainly composed of cellulose or gelatinized starch material that is substantially soluble, dispersible or disintegrable in water so that the casing is capable of quickly dissolving and/or disintegrating in gastric or ruminal juice thereby exposing the calcium source to the juice.

2. The preparation according to claim 1, wherein the cellulose material is selected from the group consisting of paperboard, cardboard, millboard, and pasteboard, sized with a water soluble edible size.

3. The preparation according to claim 1, wherein the proportion of calcium chloride constitutes 10-99% by weight and the proportion of calcium propionate constitutes 90-1% by weight of the total mixture of calcium chloride and calcium propionate.

4. The preparation according to claim 1, wherein the mixture of calcium chloride and calcium propionate is in a proportion of calcium chloride of 50-95%, by weight and a proportion of calcium propionate of 50-5%, by weight of the total mixture of calcium chloride and calcium propionate.

5. The preparation according to claim 1, wherein the casing contains at least 40 grams of calcium.

6. The preparation according to claim 1, further comprising a magnesium compound.

7. The preparation according to claim 1, further comprising a magnesium compound selected from MgO and $MgSO_4$.

8. The preparation according to claim 1, further comprising vitamin $D_3$.

9. The preparation according to claim 1, in a unit dosage form adapted for administration to a mammal and in an amount sufficient for the prevention and/or treatment of milk fever (Parturient Paresis) in said mammal.

10. The preparation according to claim 9 in a form and quantity sufficient for prevention and/or treatment of milk fever (Parturient Paresis) in a ruminant.

11. The preparation according to claim 10, in a form and quantity sufficient for prevention and/or treatment of milk fever (Parturient Paresis) in a dairy cow.

12. The preparation according to claim 1, wherein the cellulose material is paperboard, cardboard, millboard, or pasteboard.

13. The preparation according to claim 1, wherein the cylindrical casing is in the form of a tube and is provided with at least one weakened line circumferentially around its periphery in the form of a rolled or cut grove or an array of perforation points or narrow circumferential slots.

14. The preparation according to claim 1, wherein the cylindrical casing is in the form of a cylindrical tube and is closed at each end with a cap or a disc of cellulose or gelatinized starch material, and a rim at the one end of the cylindrical tube is bent or beaded inwards so as to provide a rounded outer end and an inner head or ledge on which an internal placed circular dosing disc abuts, whereas the other end of the cylindrical tube is closed by a circular disc inserted into the bore of the tube and attached therein with wax, paraffin or water soluble glue.

15. The preparation according to claim 1, wherein the cylindrical casing is in the form of a cylindrical tube and is closed at each end with a cap or a disc of cellulose or gelatinized starch material, a rim at the one end of the cylindrical tube is bent or beaded inwards so as to provide a rounded outer end and an inner bead or ledge on which an internal placed circular closing disc abuts, whereas the other end of the cylindrical tube is closed by a circular disc inserted into the bore of the tube and attached therein with wax, paraffin or water soluble glue, and the cylinder is provided with at least one weakened line circumferentially around its periphery in the form of a rolled or cut grove or an array of perforation points or narrow circumferential slots.

16. A preparation in a unit dosage form capable of and adapted for administration to a mammal, and comprising a calcium source and a casing, wherein
   (1) the calcium source is adapted to and capable of being administered orally as a bolus to a mammal, the calcium source being present in an amount sufficient for the prevention and/or treatment of calcium deficiency in the mammal,
   (2) the calcium source is in an essentially dry powder form, essentially free of any fatty or greasy substance,
   (3) the calcium source is enclosed in a substantially water soluble, dispersible or disintegrable cylindrical casing mainly composed of cellulose or gelatinized starch material,
   (4) said casing is a cylindrical tube closed at both ends with a cap or disk of cellulose or gelatinized starch material;
   (5) the calcium source comprises a compacted or compressed dry powder mixture of calcium chloride and calcium propionate containing at least 30 grams of calcium,
   (6) the casing is capable of and adapted to quickly dissolve and/or disintegrate in gastric or ruminal juice thereby exposing the calcium source to the juice, and
   (7) the individual particles of said powdered calcium source are not enveloped in or impregnated with any fatty or greasy substance to an extent that will hamper the calcium source from quickly dissolving or leaching into the gastric or rumen juice of an animal, when ingested.

17. The preparation according to claim 16, wherein
   the mixture of calcium chloride and calcium and calcium propionate is in a proportion of calcium chloride of 50-95%, by weight and a proportion of calcium propionate of 50-5%, by weight of the total mixture of calcium chloride and calcium propionate; and
   the casing contains at least 40 grams of calcium.

* * * * *